United States Patent [19]

Svedman

[11] Patent Number: 5,441,490
[45] Date of Patent: Aug. 15, 1995

[54] TRANSDERMAL PERFUSION OF FLUIDS

[75] Inventor: Pal Svedman, Malmoe, Sweden

[73] Assignee: Principal AB, Malmo, Sweden

[21] Appl. No.: 84,267

[22] PCT Filed: Jan. 7, 1992

[86] PCT No.: PCT/EP92/00029
   § 371 Date: Nov. 23, 1993
   § 102(e) Date: Nov. 23, 1993

[87] PCT Pub. No.: WO92/11879
   PCT Pub. Date: Jul. 23, 1992

[30] Foreign Application Priority Data

Jan. 9, 1991 [SE] Sweden ............... 9100058
Apr. 8, 1991 [SE] Sweden ............... 9101022

[51] Int. Cl.$^6$ ........................... A61M 35/00
[52] U.S. Cl. ................ 604/289; 604/290; 604/200; 128/743
[58] Field of Search ........... 604/115, 200, 201, 204, 604/289, 290, 29; 128/743

[56] References Cited

U.S. PATENT DOCUMENTS 1,348,504  12/1969  Austin .
2,743,723   5/1956  Hein .................... 604/115
3,486,504  12/1969  Austin, Jr. ............. 604/289

FOREIGN PATENT DOCUMENTS

21926/88  of 0000  Australia .
983602    6/1951   France .
2303972  10/1976   France .
1238616   4/1967   Germany .

OTHER PUBLICATIONS

English-language translation of column 1, line 43 to column 2, line 39 of German Patent No. 1 238 616 (1 page), Apr. 13, 1967.
English-language translation of p. 1, lien 39 to p. 2 line 34 of French patent No. 75 07924 (2 pages), Oct. 18, 1976.
English-language translation of column 2, lines 3 to 38 of French patent No. 983 602 (1 page), Jun. 26, 1951.
"Suction Blister Device for Separation of Viable Epidermis from Dermis", by Urpo Kiistala, Journal of Investigative Dermatology, vol. 50, No. 2, pp. 129–137.
"The Suction Blister Method", by Urpo Kiistala, University of Helsinki Hospital, May 21, 1976, pp. 3–37.
"Biochemical Composition of Suction Blister Fluid Determined by High Resolution Multicomponent Analysis (Capillary Gas Chromatography-Mass Spectrometry and Two-Dimensional Electrophoresis)" by Gunnar Volden, et al., Journal of Investigative Dermatology, vol. 75, No. 5, 1980, pp. 421–424.
"Pharmacokinetic Studies of Antibacterial Aents Using the Suction Blister Method", by Johan N. Brunn, et al., Scandinavian Journal of Infectious Diseases Supplement, 74, 1991, pp. 49–53.
"Suction Blister Device with Regulation of Temperature: Demonstration of Histamine Release and Temperature Change in Cold Urticaria", by H. Neittaanmaki, et al., Archives of Dermatological Research, 276, 1984, pp. 317–321
"Some Factors Affecting the Speed of Suction Blister Formation in Normal Subjects", by R. D. G. Peachey, British Journal of Dermatology, 84, 1971, pp. 435–446.

*Primary Examiner*—Jerome L. Kruter
*Attorney, Agent, or Firm*—Michael A. Kaufman; Walter H. Dreger

[57] ABSTRACT

An apparatus is provided for removing a small area of epidermis from the skin to expose an intact area of dermis and subsequently deliver a liquid in contact with the exposed dermis. This method of delivery allows the rate of absorption of substances into the body to be enhanced by removal of the epidermis. A preferred embodiment removes the epidermis by forming a suction blister, the apparatus having a housing attached to the skin adhesively to define a chamber in which suction is applied. Suction is applied to the chamber without connection to an external source of suction by means of an evacuated cell separated from the chamber by a disruptable membrane. A tubular member is actuated to rupture the membrane, disrupt the blister and deliver liquid to the chamber in successive stages of operation of the apparatus.

25 Claims, 11 Drawing Sheets

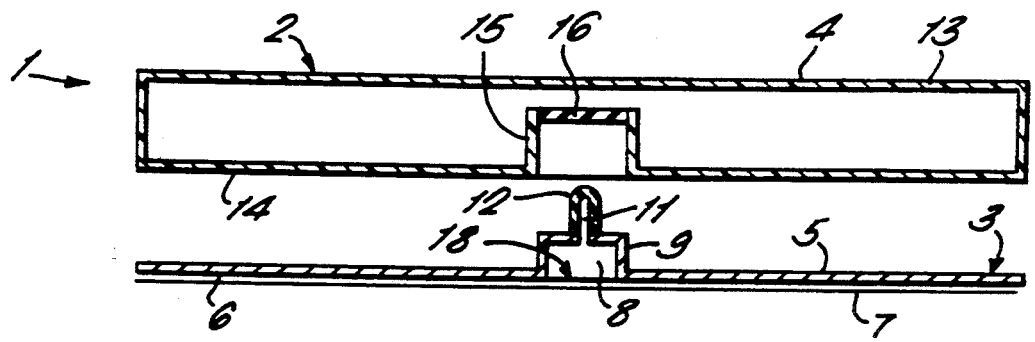
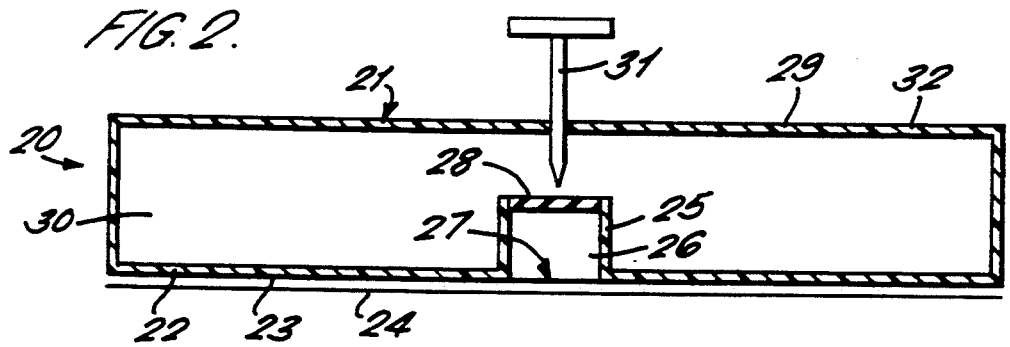
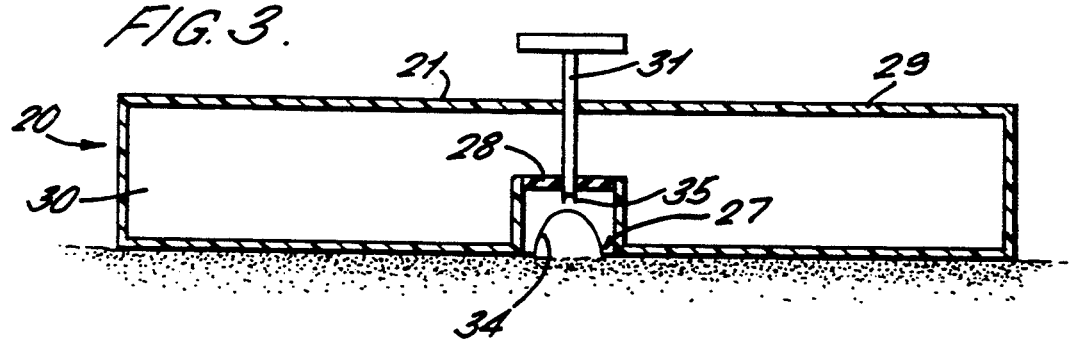
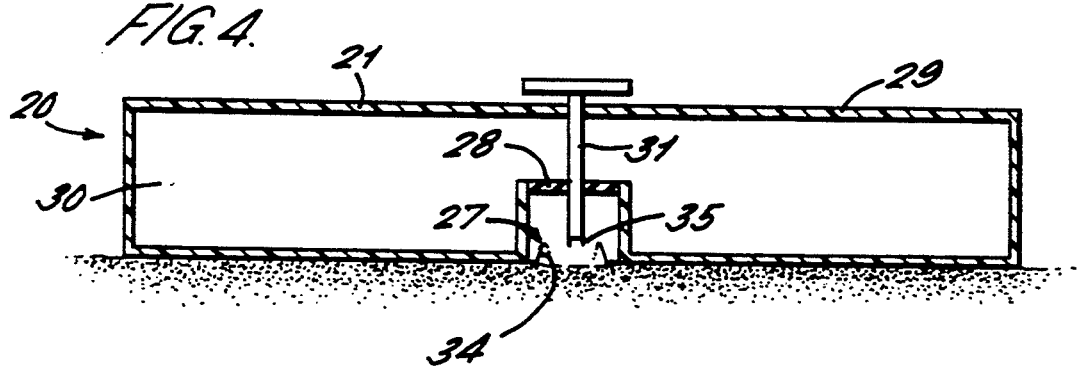

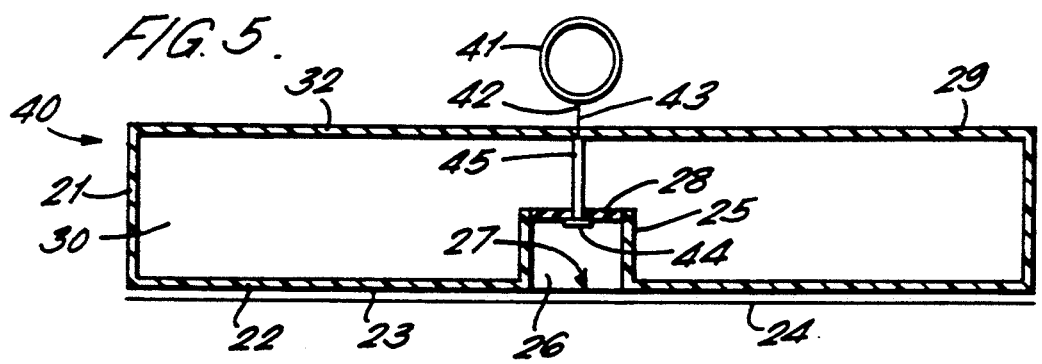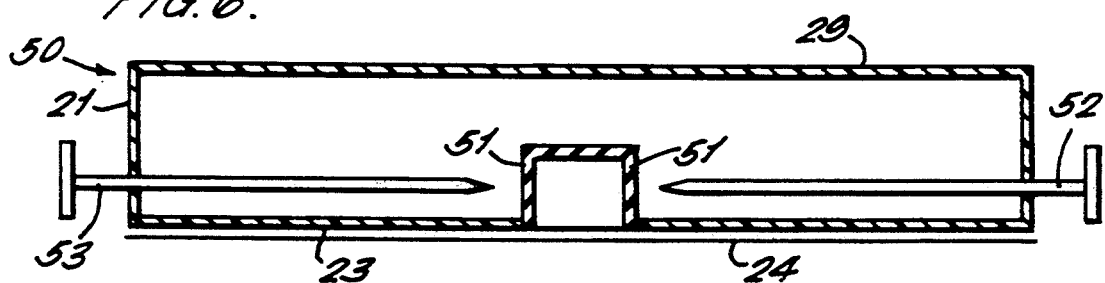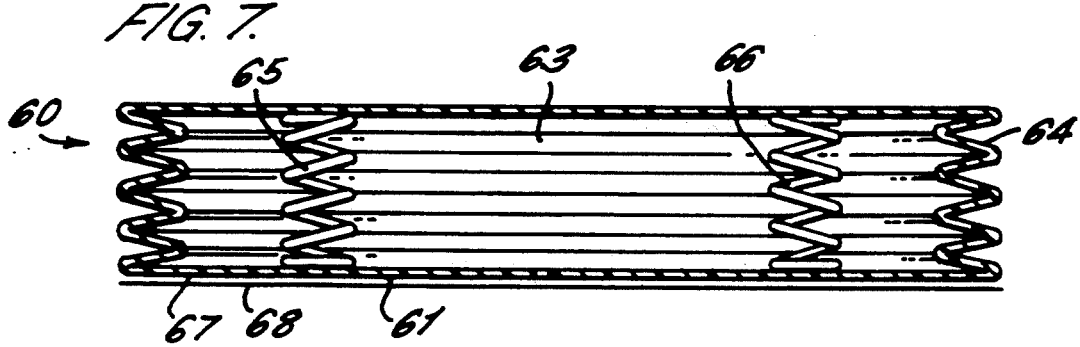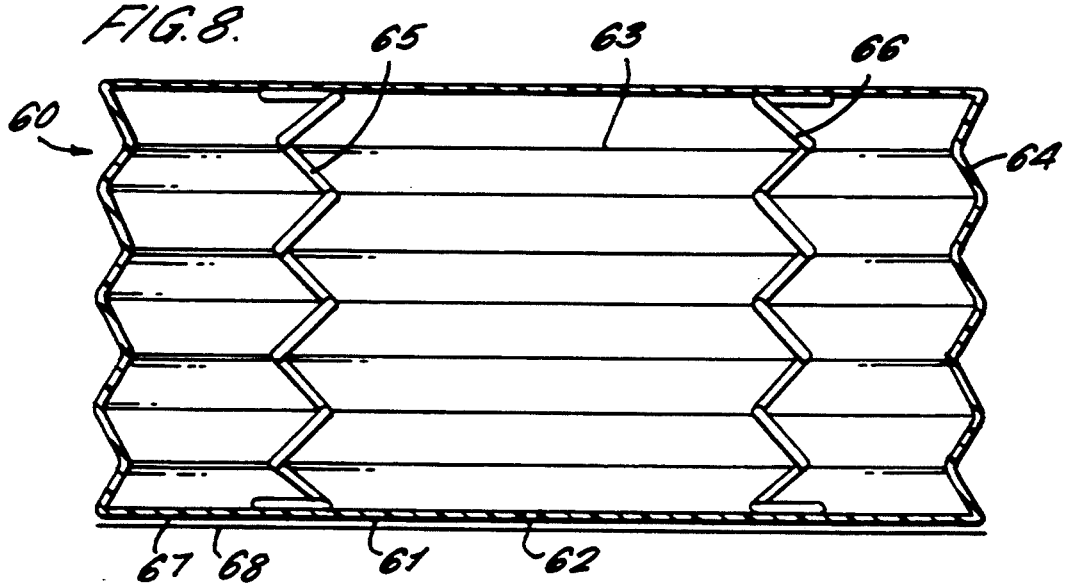

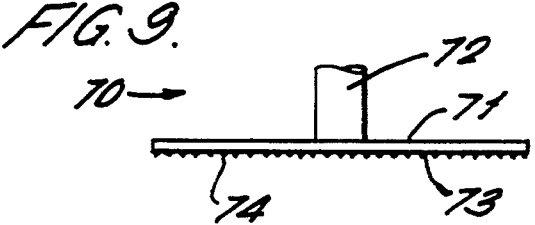
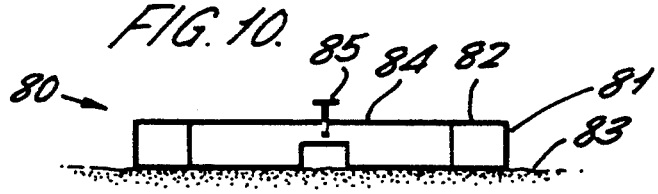
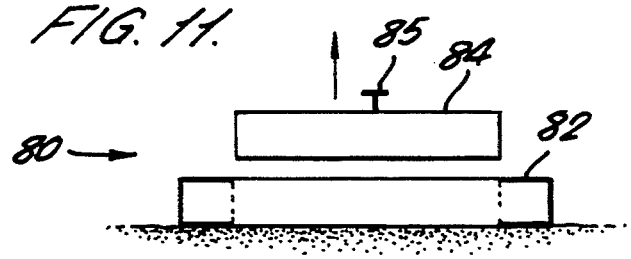
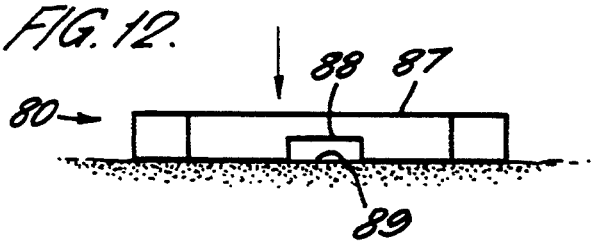
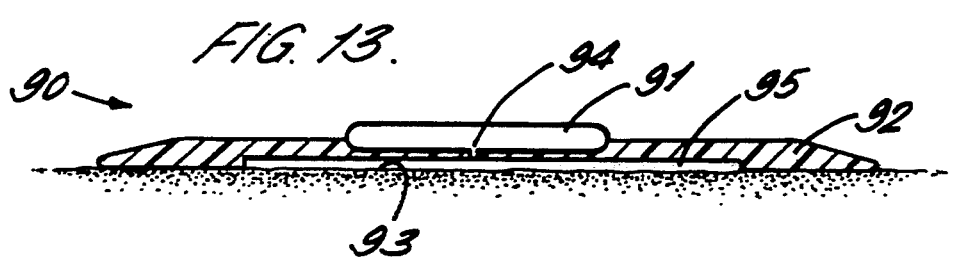

TRANSDERMAL PERFUSION OF FLUIDS

FIELD OF THE INVENTION

This invention relates to transdermal perfusion of fluids through the skin of the human or animal body and in particular but not exclusively to apparatus for de-epithelialising the skin by the suction blister method to enable perfusion to take place directly via the dermis layer.

BACKGROUND OF THE INVENTION

The transdermal perfusion of fluids for drug delivery has in recent years become an increasingly favoured alternative to intravenous or oral drug delivery. The technique has however found limited application because the epidermis (outer skin layer) forms an effective barrier to the perfusion of substances and in particular drugs having a large molecular size.

Various techniques have been proposed to enhance transdermal delivery including iontophoresis and the use as chemical enhancers. (Chemical enhancement is for example described in Int. J. Pharm. 1989, 49, 199–201 and Iontophoresis in J. Pharm. Sci. 1990, 79, 490–93). Mechanical stimulation for instance by ultrasound has also been used to enhance transdermal delivery. (Use of ultrasound is for example described in Pharm. Res. 1992, 9, 559–564). There remains a need however to provide a more effective transdermal technique particularly for peptides and hormones which hitherto have not been capable of being transdermally administered.

SUMMARY OF THE INVENTION

It is also known from US-A-3486504 to provide a resilient housing with an air release valve which can be held against an infected skin area by suction. A medicated and absorbent dressing within the housing is thereby held in contact with the skin.

It is also known in the field of skin grafting to remove portions of the epidermis to expose the dermis layer of skin by the application of suction in which a partial vacuum of about 200 mm of mercury applied for a period of two or three hours has the effect of delaminating the epidermis from the dermis to form a blister containing a clear blister fluid. (A suction blister method is for example described by Kiistala U, "The suction blister method for the in vivo separation of epidermis from dermis in human skin", Thesis, Univ of Helsinki, 1976). Such blisters have a roof which comprises the epidermis and can easily be removed for skin grafting.

According to the present invention there is disclosed apparatus for use in transdermal perfusion of fluids through the skin of the human or animal body, the apparatus comprising a housing attachable to the body and having a contact surface which in use is held in contact with a portion of skin, the housing defining a chamber and the contact surface defining an aperture communicating with the chamber, and fluid supply means operable during a perfusion phase of operation of the apparatus to supply fluid to the chamber characterised in that the apparatus further comprises de-epithelialising means operable during a preparatory phase of operation of the apparatus to expose an area of dermis of the skin at a treatment site which is accessible via the aperture such that subsequently during the perfusion phase direct contact is made between fluid in the chamber and the dermis.

An advantage of such apparatus is that it allows a drug to be administered directly to an exposed dermis layer of the skin so that perfusion then proceeds in a manner which is not dependent upon any property of the epidermis. In particular the apparatus can be used on different parts of the body without needing to take account of the variation in thickness of the epithelium. A further advantage is that the micro circulation in the exposed dermis is found to be enhanced by the blister forming procedure and this hyperaemia is found to persist for some days after de-epithelialisation of the dermis and this effect is believed to assist the perfusion process.

The fluid may be a liquid, gel or cream.

The de-epithelialising means may comprise suction means operable to form a partial vacuum in the chamber during a blister forming period in which an area of epithelium of the skin at the treatment site is separated from the dermis.

An advantage of the use of such suction means is that the formation of a skin blister by suctioning is a painless and minimally invasive procedure which heals rapidly and without leaving a scar. The healing process is such that the perfusion of drugs through the dermis does not become affected by the growth of a new epithelial barrier for at least four days after formation of the blister. This period can be extended by the application of suitable drugs which may be administered orally or otherwise.

Preferably the housing is cooperable with the skin to form a closed compartment of which the chamber constitutes at least a part and comprises sealing means operable between the contact surface and an annular area of skin peripheral to the treatment site whereby the partial vacuum is maintainable by substantially preventing the ingress of air during the blister forming period.

It is therefore not necessary for the chamber to remain connected to external apparatus providing suction so that a patient may be ambulatory and continue with normal physical activity during the two to three hours in which a suction blister is formed.

Conveniently the suction means comprises a cell defining a space within which a partial vacuum is formed and disrupting means operable to disrupt a membrane partitioning the space from the chamber.

It is therefore not necessary for the patient to be connected at any stage to any external suction device since partial vacuum may be introduced into the cell before attachment of the apparatus to the patient and partial vacuum subsequently applied to the chamber by subsequent disruption of the membrane.

The cell may be provided with a valve facilitating evacuation of air to create a partial vacuum within the space prior to operation of the disrupting means. A syringe or pump may be connected via the valve to the cell to provide a partial vacuum and may then be disconnected before the apparatus is applied to the patient.

The apparatus may alternatively comprise expanding means operable to expand the volume of the chamber to thereby create a partial vacuum.

Preferably the apparatus comprises blister disruption means operable to open the suction blister by penetrating, bursting or removing the detached area of epithelium constituting a roof of the blister.

The apparatus may thereby remain in situ whilst the blister is opened to provide access to the de-epithelialised dermis.

An actuator may be provided to actuate the blister disruption means and also by subsequent movement of the actuator to actuate the fluid supply means.

The actuator may also be further operable to actuate the suction means.

A single actuator can therefore be used to operate the apparatus in its successive modes of operation.

Preferably the sealing means comprises an adhesive layer operable to sealingly secure the contact surface to an annular area of skin peripheral to the treatment site.

According to a further aspect of the present invention there is disclosed apparatus for use in the formation of a suction blister on the skin of the human or animal body, the apparatus comprising a housing attachable to the body and having a contact surface which in use is held in sealing contact with the skin, the housing defining a chamber and the contact surface defining an aperture communicating with the chamber, and the apparatus further comprising suction means operable to form a partial vacuum in the chamber and thereby form a suction blister at a treatment site which is accessible via the aperture, characterised by the housing being cooperable with the skin to form a closed compartment of which the chamber constitutes at least a part and by comprising sealing means operable between the contact surface and the skin whereby the partial vacuum is maintainable by substantially preventing the ingress of air during a blister forming period.

An advantage of such apparatus is that it is not necessary for a patient to remain connected to a suction device during the suction blister forming period. The patient may therefore be ambulatory and may continue with normal physical activity.

The suction blister so formed may be used either for the sampling of blister fluid for subsequent analysis or the blister may be opened or removed to expose de-epithelialised dermis through which a drug may be perfused by the application of a suitable drug delivery mechanism.

Particular embodiments of the present invention will now be disclosed by way of example only and with reference to the accompanying drawings of which:

BRIEF DESCRIPTION OF THE DRAWINGS

FIG. 1 is a sectioned elevation of a first apparatus for forming a suction blister;

FIG. 2 is a sectioned elevation of a second apparatus for forming a suction blister and having an actuator pin;

FIG. 3 is a sectioned elevation of the apparatus of FIG. 2 showing the actuator pin in an advanced position in readiness to disrupt a suction blister;

FIG. 4 is a sectioned elevation of the apparatus of FIGS. 2 and 3 showing the actuator pin in a further advanced position in which the blister is disrupted to expose the dermis;

FIG. 5 is a sectioned elevation of a third apparatus for forming a suction blister and having a pull ring actuator;

FIG. 6 is a sectioned elevation of a fourth apparatus for forming a suction blister and having laterally disposed actuator pins;

FIG. 7 is a sectioned elevation of a fifth apparatus for forming a suction blister and comprising a sprung bellows shown in a compressed state;

FIG. 8 is a sectioned elevation of the apparatus of FIG. 7 showing the sprung bellows in an expanded state;

FIG. 9 is a sectioned elevation of a sixth apparatus for removing an area of epidermis by grinding;

FIG. 10 is a sectioned elevation of a seventh apparatus for use in transdermal perfusion of a drug;

FIG. 11 is a sectioned elevation of the apparatus of FIG. 10 showing removal of a de-epithelialisation component of the apparatus;

FIG. 12 is a sectioned elevation of the apparatus of FIGS. 10 and 11 in which the de-epithelialisation component is replaced by a drug delivery module;

FIG. 13 is a sectioned elevation of an alternative drug delivery module for use with the apparatus of FIGS. 10 to 12;

DETAILED DESCRIPTION OF THE PREFERRED EMBODIMENTS

Figure 14:
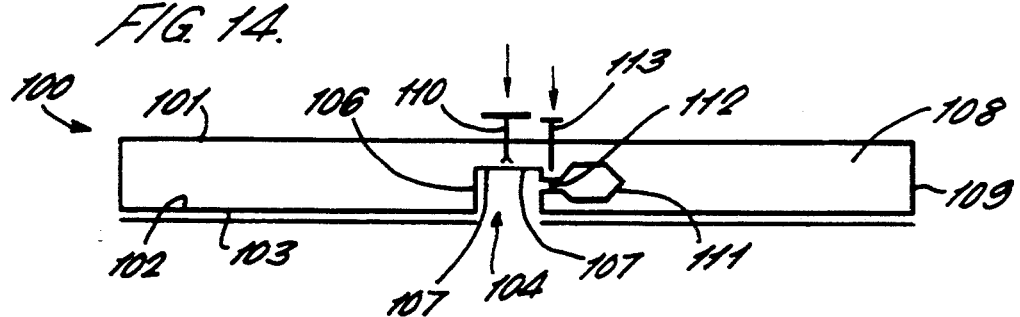
FIG. 14 is a sectioned elevation of an eighth apparatus for transdermal delivery of a drug including means for forming a suction blister, disrupting the blister and applying the drug directly to the exposed dermis.

In FIG. 1 a first apparatus 1 comprises a housing 2 of two-part construction. The housing 2 consists of a disc 3 and an evacuated cell 4 which is similarly of disc-shape and fits onto an upper surface 5 of the disc in use.

The disc 3 is formed of a rigid transparent plastics material and has a lower surface 6 which is coated with adhesive and prior to use is protected by a peel-off paper film 7. The disc 3 is centrally recessed to define a cup-shaped chamber 8 within a cylindrical formation 9 which projects upwardly of the upper surface 5. A cannula 10 projects from the cylindrical formation 9 in a direction away from the disc 3 so as to define a duct 11 communicating with the chamber 8. The cannula 10 is shown in FIG. 1 in its pre-use configuration in which it is externally covered by a closed rubber sleeve 12.

The cell 4 is formed of a rigid transparent plastics material and encloses a space 13 which is provided at manufacture with a partial vacuum of 200 mm of mercury.

The cell 4 has a lower face 14 which is centrally recessed by a cylindrical formation 15 within which the cylindrical formation 9 of the disc 3 is a sliding fit. The cylindrical formation 15 is closed by a disruptable membrane 16 formed of rubber.

The disc 3 is of 50 mm diameter and defines a central aperture of 5 mm diameter communicating with the chamber 8.

In use the paper film 7 is peeled off and the disc 3 is presented to an area of skin of the patient. The disc 3 is pressed onto the skin such that lower surface 6 is adhesively secured against the skin and forms an airtight seal. The cell 4 is advanced onto the disc 3 such that cylindrical formation 15 fits over the cylindrical formation 9 and the cannula 10 ruptures both the rubber sleeve 12 and membrane 16 to establish communication via the duct 11 between the space 13 and the chamber 8. A partial vacuum is thereby applied within the chamber 8 to an area of skin within aperture 18. The apparatus 1 is held in this position adhesively for two to three hours during which time a suction blister is formed within the chamber 8. Formation of the blister can be observed by inspection through the transparent material forming the cell 4 and disc 3. The apparatus is then removed from the skin by first removing the cell 4 to release the partial vacuum within chamber 8 and then peeling the disc 3 away from the skin.

The exposed blister may then be broken or removed to gain access for transdermal delivery of a drug to the exposed skin dermis or the blister fluid may be sampled for subsequent analysis.

A second apparatus 20 shown in FIG. 2 comprises a housing 21 which includes a transparent disc-shaped base 22 defining a contact surface 23. The contact surface 23 has an adhesive coating which is protected prior to use by a peel-off paper film 24. The contact surface 23 is centrally recessed by a cylindrical formation 25 defining a cylindrical chamber 26, the contact surface 23 defining a circular aperture 27 of 5 mm diameter communicating with the chamber 26. The chamber is closed at its other end by a disruptable rubber membrane 28.

The housing 21 further comprises a cell 29 of transparent plastics material which is closed by membrane 28 to enclose a sealed space 30. The space 30 is evacuated at manufacture to provide a partial vacuum of 200 mm of mercury.

An actuator pin 31 projects sealingly through an outer wall 32 of cell 29. Actuator pin 31 is axially movable towards the membrane 28 so as to form a central puncture in use.

In use the film 24 is peeled off and the contact surface 23 is adhesively secured to the skin of the patient so as to form an airtight seal. The chamber 26 is then closed by an area of skin defined within the aperture 33. Actuator pin 31 is then advanced so as to rupture the membrane 28 and air moves through the ruptured membrane to equalise pressure in the space 30 and chamber 26. A partial vacuum is thereby applied to the area of skin exposed within the aperture 33. The chamber 26 and the space 30 together constitute a closed compartment in which a partial vacuum is maintained so long as the ingress of air is prevented by the airtight seal between the contact surface and the skin. The apparatus 20 is left in situ for a period of about two hours during which time the formation of a suction blister 34 is observed through the transparent housing 21 as shown in FIG. 3. In FIG. 3 the actuator pin 31 is shown in an orientation in which it is rotated through 90° relative to the position shown in FIG. 2 thereby revealing cutting edges 35 which disrupt the blister 34 as shown in FIG. 4 when the actuator pin is further advanced.

The contents of the blister 34 may be sampled and analysed or a skin patch (not shown) may be applied over the site of the broken blister to apply a liquid drug to be perfused through the exposed dermis.

A third apparatus 40 is shown in FIG. 5 and will be described using corresponding reference numerals to those of FIGS. 2, 3 and 4 where appropriate for corresponding elements.

Apparatus 40 similarly has a transparent housing 21 with a cell 29 enclosing an evacuated space 30 and suction is applied through aperture 27 in contact surface 23 by creating a partial vacuum in chamber 26 by disrupting a membrane 28. The apparatus 40 includes a pull-ring actuator 41 to which is attached a first end 42 of a wire 43 of which a second end 44 is anchored in the membrane 28. The wire 43 is enclosed within a sheath 45 which is sealed to both the outer wall 32 of the cell 29 and the membrane 28.

In use the pull-ring actuator 41 is pulled to displace the wire 43 so that the second end 44 is pulled through the membrane 28 leaving a hole through which air flows between the chamber 26 and space 30. A partial vacuum is thereby applied to the chamber 26 for the formation of a skin blister. The partial vacuum then persists in the closed compartment constituted by chamber 26 and space 30 so long as an airtight seal across the aperture is provided by adhesive contact with the skin.

A fourth apparatus 50 is shown in FIG. 6 and will be described using corresponding reference numerals to those of FIG. 2 where appropriate for corresponding elements.

Apparatus 50 comprises a transparent housing 21 having a contact surface 23 and an evacuated cell 29. A cylindrical formation 25 defines a chamber 26 which is closed by adhesion of the contact surface 23 to an area of skin and partial vacuum within the chamber 26 is then applied by disrupting side walls 51 of the cylindrical formation 25 by means of laterally extending actuator pins 52 and 53. Operation of the apparatus 50 is in other respects similar to that of apparatus 20.

In FIG. 7 a fifth apparatus 60 comprises a disc-shaped base 61 defining a central aperture 62 which communicates directly with a chamber 63 defined by a bellows 64. The bellows 64 is biassed by coil springs 65 and 66 into an extended position as shown in FIG. 8. The apparatus 60 is normally stored in its compressed state as shown in FIG. 7 and the base 61 defines a contact surface 67 which is adhesively coated and is provided pre-use with a protective film 68. The film 68 closes aperture 61 in this condition to prevent ingress of debris during storage.

The bellows 64 is clamped in its compressed condition by means of a clamp (not shown) and an actuator (not shown) is provided to release the clamp to allow the bellows to expand to its expanded configuration shown in FIG. 8.

In use the film 68 is removed and the contact surface 67 applied to the skin so that aperture 62 is closed in airtight manner by an area of skin. The actuator is operated to unclamp the bellows 64 and the bellows expand by spring action to thereby increase the volume of chamber 63 and this results in the creation of a partial vacuum which is applied to the area of skin exposed by aperture 62. The apparatus 60 is left in situ for a period of about two hours and may then be removed first by compressing the bellows to its original shape to remove the partial vacuum and then peeling off the contact surface from the skin. The blister may then be broken or removed and a transdermal skin patch applied to the exposed dermis.

A sixth apparatus 70 is shown in FIG. 9 and comprises a disc 71 which is axially mounted on a shaft 72. The disc 71 has a flat contact surface 73 from which a plurality of sharp edged protrusions 74 project towards the skin. The protrusions 74 have a height corresponding to the depth of epidermis and in use the contact surface is placed against the skin and the disc rotated by means of shaft 72 to thereby form incisions in the epidermis. The apparatus 70 is then removed and a skin patch containing a drug is then applied to the area of skin in which the incisions are formed.

A seventh apparatus 80 is shown in FIGS. 10, 11 and 12 and comprises a housing 81 consisting of an annular frame 82 which is adhesively secured to an area of skin 83 in use. A de-epithelialising apparatus 84 is releasably locatable within the annular frame 82 and in FIGS. 10 and 11 the de-epithelialising apparatus 84 is of the type described above with reference to FIGS. 2, 3 and 4 in which a suction blister is formed and ruptured by actuation of an actuator pin 85. In FIG. 10 the de-epithelialising apparatus 84 is shown in situ prior to use. In FIG. 11 the de-epithelialising apparatus is shown separated from the frame 82 after formation and rupturing of the blister (not shown). FIG. 12 shows a drug delivery module 86 located within the frame 82 following removal of the de-epithelialising apparatus 84. The drug delivery module 86 comprises a disc-shaped casing 87 having a central drug compartment 88 which includes a semi-permeable membrane 89 through which the drug exudes at a predetermined rate. (Detail of the ruptured blister is omitted from FIG. 12).

The casing 87 is configured to be a close fit within the frame 82 and to locate the membrane 89 over the location of the area of skin which is de-epithelialised by the apparatus 84.

The diameter of the membrane 89 is greater than the diameter of the de-epithelialised skin patch to take account of any errors in positioning.

The apparatus of FIGS. 10 to 12 may alternatively utilise the apparatus of FIG. 9 in achieving de-epithelialising of the skin, the apparatus 70 being located within the frame 82 and removed prior to insertion of drug delivery module 86.

An alternative drug delivery module 90 is shown in FIG. 13 and comprises a reservoir 91 containing a volume of drug, the reservoir being held by an annular support 92 in proximity with skin surface 93. The support 92 defines a narrow bore connecting tube 94 communicating between the reservoir 91 and a recess 95 which is defined by the support and overlays the de-epithelialised skin area. Liquid drug is progressively fed by capillary action through the connecting tube 94 into the recess and hence is perfused through the exposed dermis.

The flow of liquid through the connecting tube may be aided by the application of positive pressure to the reservoir 91.

In FIG. 14 an eighth apparatus 100 for the transdermal delivery of a drug comprises a transparent housing 101 with a disc-shaped base 102. A contact surface 103 is adhesively coated so as to adhere to a skin surface and the base defines a central aperture 104 communicating with a chamber 105 formed by a cylindrical formation 106.

The cylindrical formation 106 is closed at one end by a frangible membrane 107 which initially separates the chamber 105 from an evacuated space 108 provided by a cell 109 of the housing 101.

The frangible membrane 107 is disruptable by means of an actuator pin 110 of the type described above with reference to FIGS. 2, 3 and 4 so that actuation of the pin 110 ruptures the membrane to introduce partial vacuum into the chamber 105 during a blister forming period. Further actuation of the pin 110 advances the pin to a position in which it will disrupt the blister to expose the dermis within the chamber 105.

Apparatus 100 also comprises an integrally formed drug reservoir 111 which is normally sealed by a frangible plug 112. A drug release actuator 113 is provided for breaking the plug 112 and allowing the drug to flow into the chamber 105.

In use the apparatus 100 is placed on the skin such that adhesion between the contact surface 103 and skin provides an airtight seal across the aperture 104. The actuator pin is then advanced to disrupt the membrane 107 so that a partial vacuum is produced in the chamber 105 to form a blister. The cell and chamber together constitute a closed compartment sealed by the area of skin and in which partial vacuum persists during a blister forming period. The blister is then ruptured by further actuation of actuator pin 110 and the drug release actuator 113 is then operated to allow drug into the chamber 105. De-epithelialised dermis exposed by rupturing the blister is then exposed to the drug and transdermal perfusion then proceeds.

Figure 15:
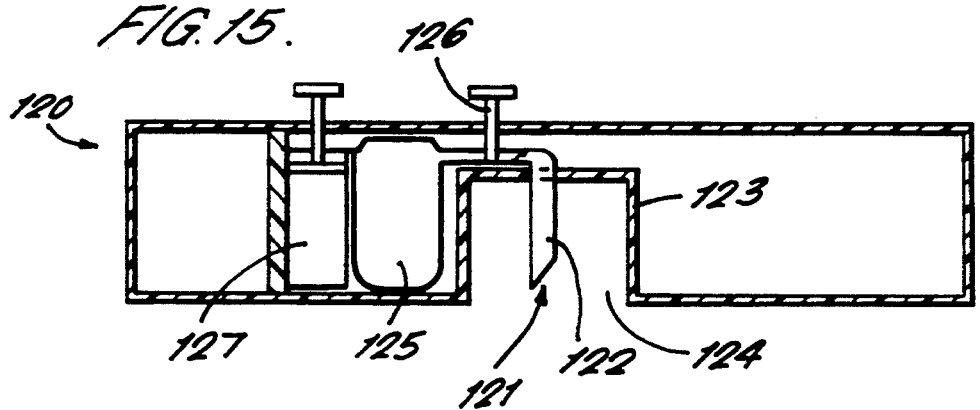
FIG. 15 is a sectioned elevation of a ninth apparatus having a cannula for drug delivery by injection.

In FIG. 15 a ninth apparatus 120 includes an apparatus for transdermal drug delivery such as that described with reference to FIG. 14 (details of such transdermal apparatus are not shown in FIG. 15) and additionally includes an injection device 121 which is operable to inject via a cannula 122 an initial dose of drug prior to de-epithelialisation and transdermal delivery by means of the transdermal apparatus using an adjacent patch of skin. Such immediate administration of a dose is useful in administering pain relief for example or control of premature muscle contractions of the uterus during pre-term labour.

Figure 16:
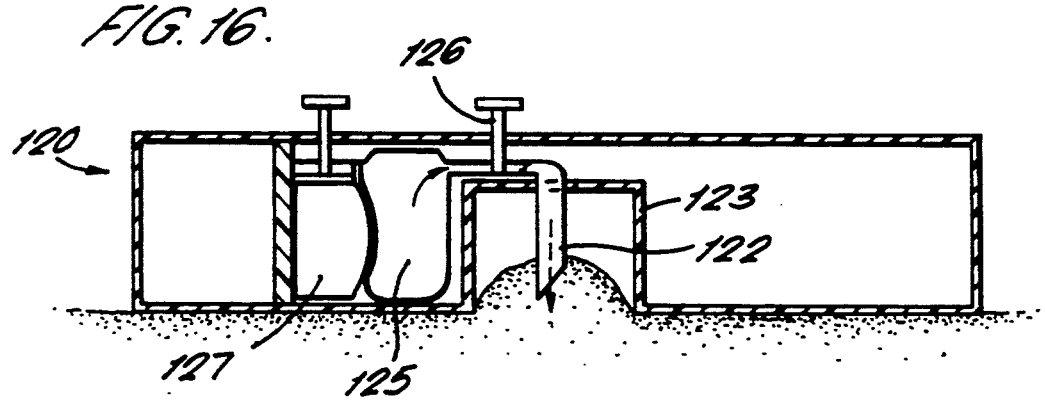
FIG. 16 is a sectioned elevation of the apparatus of FIG. 15 showing the cannula extending through the skin.

The injection device 121 comprises an additional suction cup 123 defining a suction chamber 124 to which suction is applied to immediately draw skin into the chamber as shown in FIG. 16. The cannula 122 is located within the chamber in a position such that skin drawn into the chamber by suction is penetrated. Drug is then injected through the cannula from a reservoir 125 on release of a valve 126. Drug within the reservoir 125 is pressurised by means of an expanding device 127 placed in contact with the reservoir 125 which is formed of a deformable material so as to be collapsible.

Figure 17:
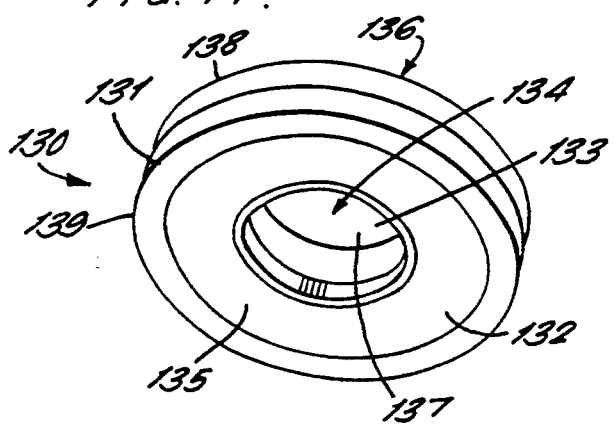
FIG. 17 is a perspective view of a tenth apparatus for transdermal delivery of a drug and showing a suction chamber in its pre-use configuration.

A tenth apparatus 130 shown in FIG. 17 comprises a housing 131 having an annular contact surface 132 defining an aperture 133. The housing 131 is centrally recessed to define a chamber 134 communicating with the aperture.

The housing 131 incorporates an annular drug reservoir 135 peripherally disposed relative to the aperture 133 and includes an evacuated cell 136 which is isolated from the chamber 134 prior to use by a disruptable membrane 137.

The housing 131 has an actuator cap 138 which is movable relative to a base portion 139 which includes the contact surface 132.

Apparatus 130 is arranged to provide for the formation and disruption of a suction blister and for subsequent drug delivery to the exposed dermis by successive actuation of the actuator cap 138.

The housing 131 is initially secured to a patch of skin such that the aperture 133 is closed in a sealed manner by an area of skin through which drug is to be transdermally delivered. The housing 131 is secured by means of a peripheral support frame (not shown).

Figure 18:
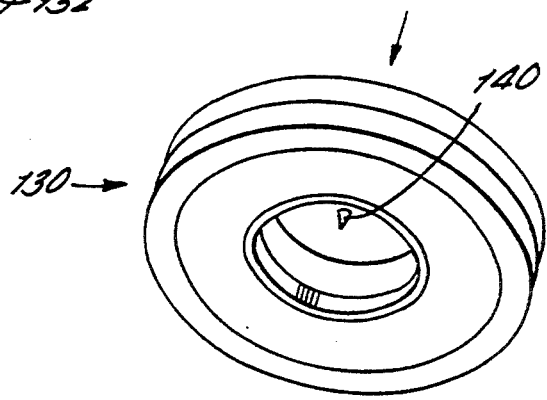
FIG. 18 is a perspective view of the apparatus of FIG. 17 showing the introduction via a cannula of partial vacuum within the suction chamber.

As shown in FIG. 18 the actuator cap 138 is pressed towards the base portion 139 so as to advance a cannula 140 so as to penetrate the membrane 137 and place the chamber 134 in communication with the evacuated cell 136. A partial vacuum is thereby created within the chamber 134 and the partial vacuum persists during a blister forming period by virtue of the contact surface 132 being sealed against the skin.

Figure 19:
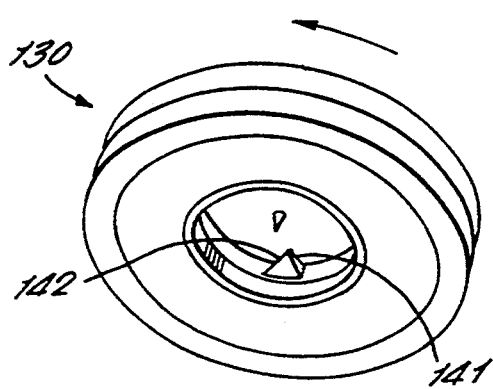
FIG. 19 is a perspective view of the apparatus of FIGS. 17 and 18 showing actuation of a blister disrupting fin.

After a period of two hours the actuator cap 138 is rotated through 45° as shown in FIG. 19 in response to which motion air is admitted to the chamber 134 through a release valve (not shown) so as to restore atmospheric pressure and a blister disrupting fin 141 moves into the chamber 134 and breaks or removes the roof of the blister formed within the chamber. The fin 141 includes an absorbent layer 142 which absorbs blister fluid released by this motion.

Figure 20:
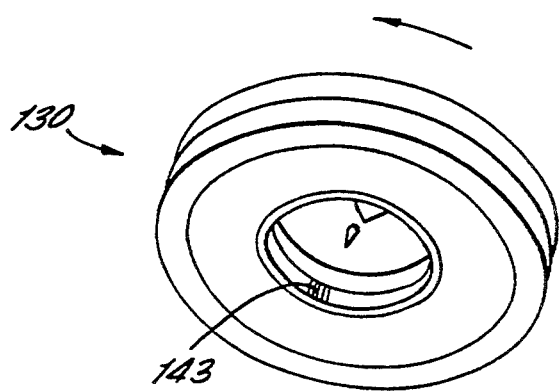
FIG. 20 is a perspective view of the apparatus of FIGS. 17 to 19 showing the opening of a valve admitting drug to the chamber.

The actuator cap 138 is again further advanced as shown in FIG. 20 through a rotational movement of 45° and this further motion opens a valve to release a liquid drug from the reservoir 135 through an outlet 143 into the chamber 134.

Transdermal perfusion of the drug through the exposed dermis of the skin then proceeds.

Figure 21:
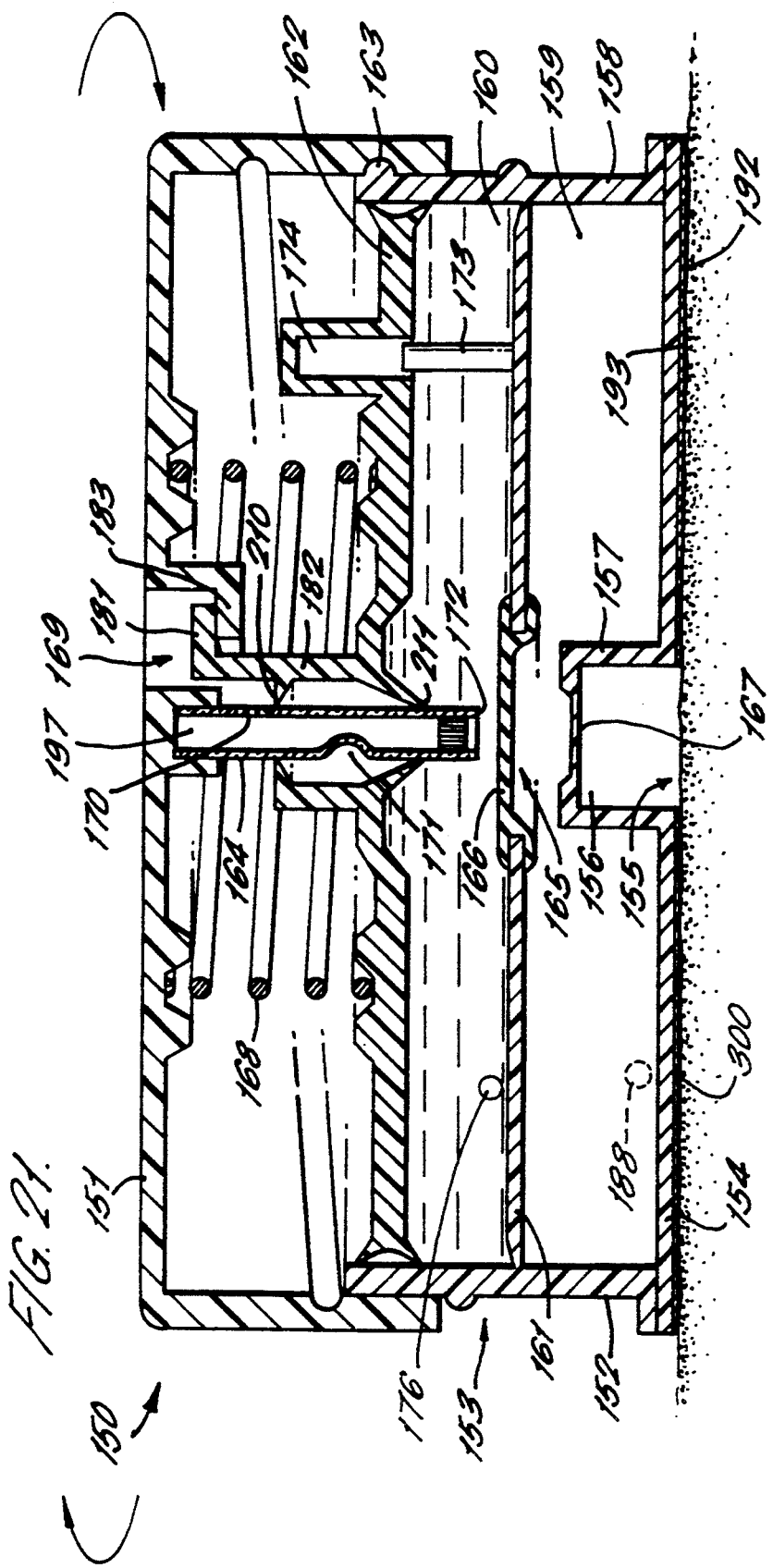
FIG. 21 is a sectioned elevation of an eleventh apparatus for transdermal drug delivery in its pre-use configuration.

An eleventh apparatus 150 shown in FIG. 21 also includes an actuator cap 151 which provides successive operations of blister formation, blister disruption and drug release by successive stages of movement of the cap relative to a base portion 152 of a housing 153. The housing 153 includes a disc portion 154 having a flat disc-shaped contact surface 192 defining a central aperture 155 of 5 mm diameter. The aperture 155 communicates with a chamber 156 defined by a cylindrical formation 157 projecting upwardly of the disc portion.

The housing 153 includes a cell 158 bounded on one side by the disc portion 154 and defining a closed space 159. The housing 153 also includes a drug reservoir 160 which is separated from the space 159 by a partition 161 extending parallel to the disc portion 154.

The volume of the drug reservoir 160 is variable by movement of a piston 162 which is movable towards the partition 161 to reduce the volume of the reservoir for the purpose of expelling liquid drug.

The housing 153 is cylindrical in shape and the actuator cap 151 is similarly cylindrical and overlays the housing, the housing and cap having cooperating screw threads 163 whereby rotation of the cap relative to the housing advances the cap towards the disc portion 154.

A hollow needle 164 is mounted axially within the cap 151 such that rotation of the cap produces axial movement of the needle relative to the housing.

In FIG. 21 the apparatus 150 is shown in its initial rest position in which the needle 164 projects sealingly through the piston 162.

The partition 161 includes a central orifice 165 which is normally sealed by a rubber plug 166. The rubber plug 166 is in axial alignment with the needle 164 and with a membrane seal 167 forming part of the cylindrical formation 157 and normally separating the chamber 156 from the space 159 within cell 158.

The piston 162 is biassed in a direction towards the partition 161 by means of a coil spring 168 and the piston is restrained against axial movement by means of a catch 169 which is releasable by rotation of the cap 151 in a manner described below.

The hollow needle 164 has a side hole 170 which in the rest position shown in FIG. 21 is located above the piston 162 so as to be outside of the drug reservoir 160. The piston is provided with upper and lower sliding seals 210,211 respectively which "bracket" the side hole 170 and prevent entry of air.

The needle 164 also has an indentation 171 located intermediate the side hole 170 and the needle tip 172.

Rotation of the piston 162 relative to the base portion 152 is prevented by means of a locating pin 173 which is received in a cooperating recess 174 of the piston.

The cell 158 is evacuated to have a partial vacuum of 200 mm of mercury.

The apparatus is prepared for use by removing a protective film to expose an adhesive coated disc portion 154 having an adhesive layer 300, the cell 158 being evacuated and the drug reservoir 160 being initially empty.

In use, the housing 153 is attached to the skin of the user such that the disc portion 154 is adhesively sealed to an annular area of skin 193 peripheral to a treatment site 196. Central aperture 155 is thereby sealed against ingress of air which thereby closes the chamber 156. Suction is applied at the treatment site 196 by actuation of the cap 151 so as to advance the needle 164 through both the rubber plug 166 and the membrane seal 167. The membrane seal 167 is formed of a frangible material which fractures and provides for the passage of air between the space 159 and the chamber 156 thereby reducing the pressure within the chamber. The rubber plug 166 maintains sealing engagement with the needle 164 so that no air enters the space 159 from the reservoir 160. Air cannot enter the chamber 156 through the needle 164 since the side hole 170 remains sealed by the seals 210,211.

A partial vacuum is maintained within the closed compartment constituted by the space 159 and the chamber 156 during a blister forming period, the ingress of air being prevented by an adhesive seal between the disc portion 154 and the annular portion of skin 193.

Figure 22:
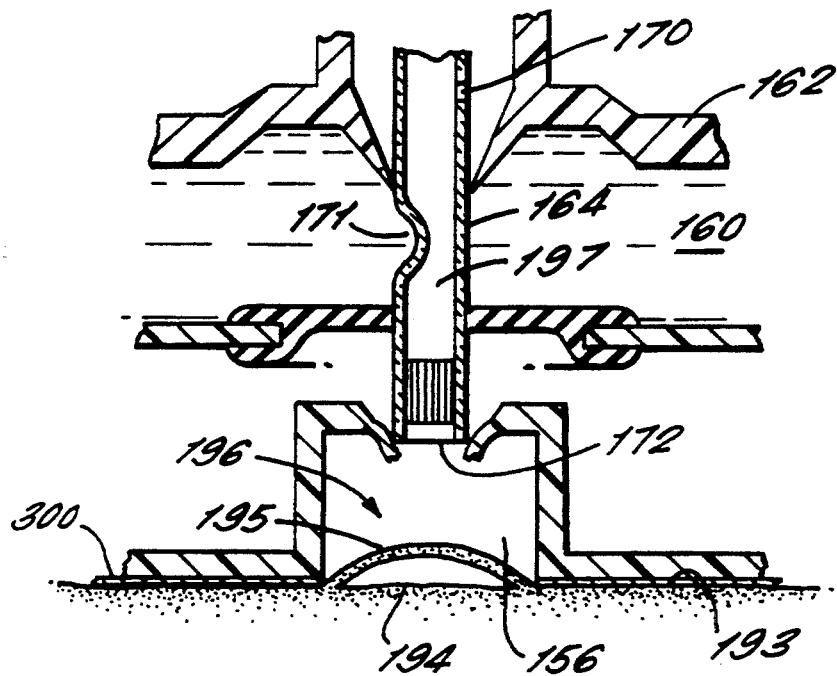
FIG. 22 is a sectioned elevation of the apparatus of FIG. 21 showing the actuation of suction means to apply partial vacuum to the skin.

The formation of a blister is illustrated in FIG. 22 which shows the position of the needle during the blister forming period. The blister consists of a raised portion of epithelium 195 which is 'delaminated' from the dermis 194 to which it is normally attached.

Figure 23:
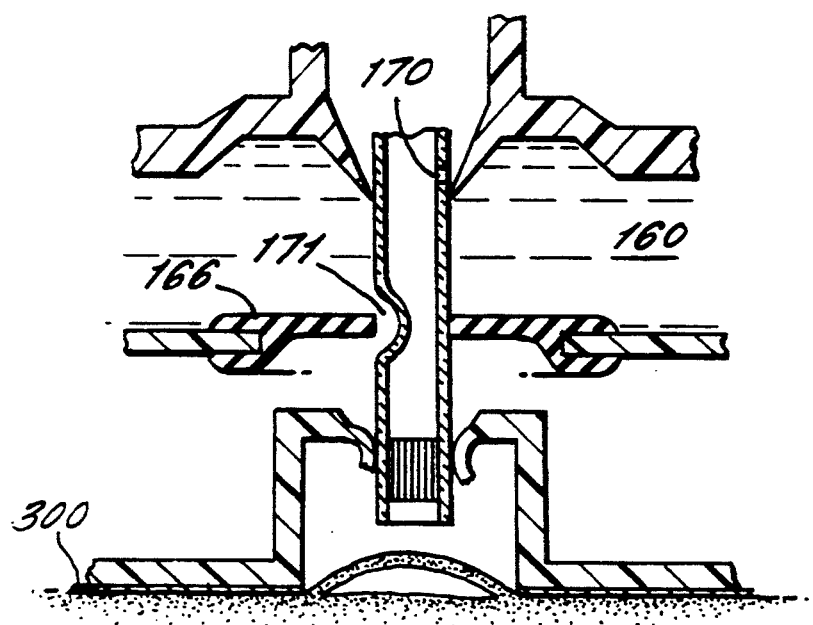
FIG. 23 is a sectioned elevation of the apparatus of FIGS. 21 and 22 showing the release of partial vacuum following formation of a skin blister.

Once a blister has been formed after a period of two hours a further rotational movement of the cap 151 is required to further advance the needle 164 to the venting position shown in FIG. 23 in which the indentation 171 comes into registration with the rubber plug 166 thereby allowing air from the reservoir 160 to enter the space 159 to restore atmospheric pressure.

Figure 27:
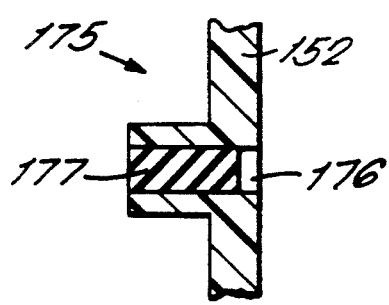
FIG. 27 is a section showing detail of a drug injection port of the apparatus of FIGS. 21 to 26.

At this stage a quantity of drug is inserted into the reservoir 160 through a drug insertion port 175 of the type shown in FIG. 27. As shown in FIG. 27 an insertion port 175 is located so as to provide a means of injecting liquid drug through the housing into the reservoir 160.

The drug insertion port 175 comprises a duct 176 communicating with the reservoir 160 and closed by a self-healing rubber bung 177 through which a syringe needle is insertable.

After filling the reservoir 160 with a liquid drug a further movement of the actuator cap 151 rotates the cap to a position in which the side hole 170 is located within the reservoir 160 and at the same time the catch 169 operates to release the piston 162. Under the action of the spring 168 the piston 162 pressurises liquid within the reservoir 160 which flows into the needle 164 through the hole 170 and emerges from the needle tip 172 into the chamber 156. By this further advancement of the needle the blister 178 is ruptured so that drug within the chamber 156 comes into contact with the exposed dermis 179 so that transdermal delivery of the drug is commenced.

Figure 24:
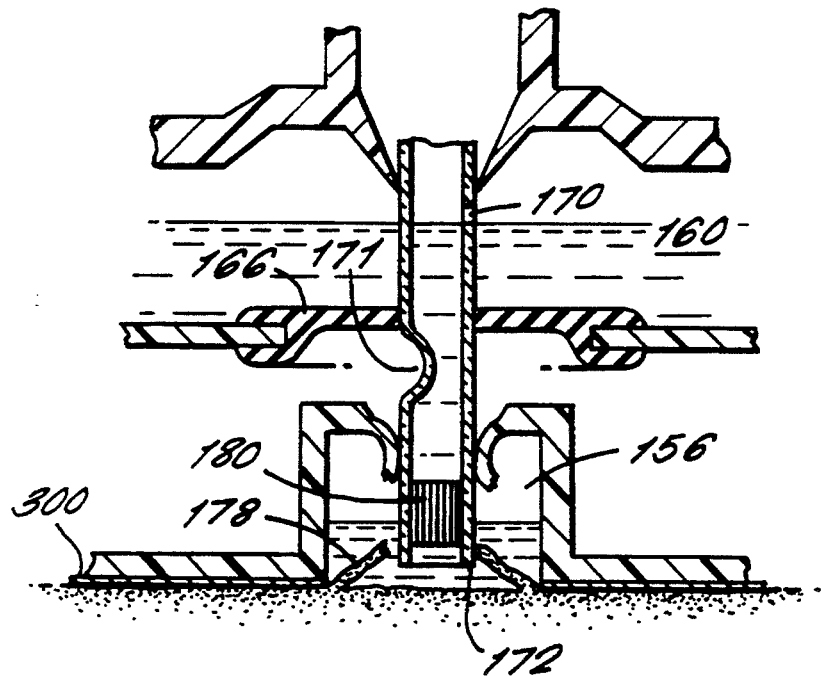
FIG. 24 is a sectioned elevation of the apparatus of FIGS. 21 to 23 showing the disruption of the blister.

As shown in FIG. 24 the needle 164 includes a microporous filter 180 adjacent the needle tip 172 by means of which the flow of liquid into the chamber 150 is restricted. This slows the rate of release of drug into the chamber 156 and ensures a gradual release of drug at a predetermined rate.

The housing 153 is held in situ for a period during which transdermal delivery proceeds and this period may extend to four days by which time the self-healing of the epidermis will begin to provide a barrier providing direct access to the dermis.

Figure 25:
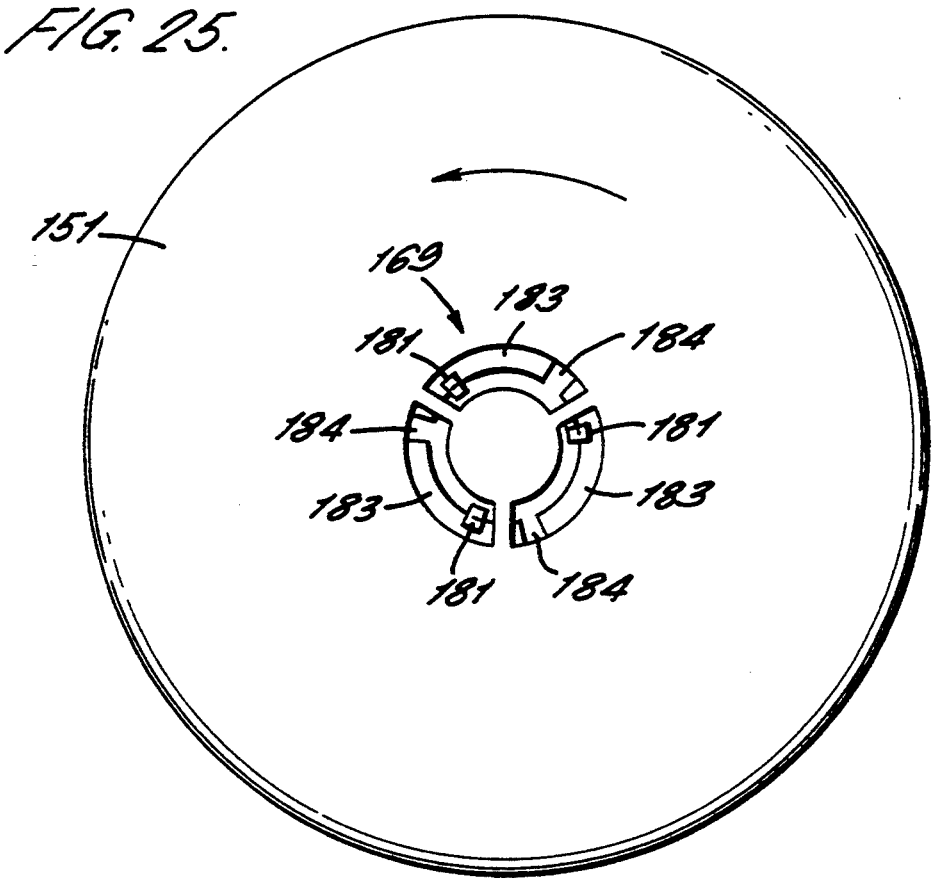
FIG. 25 is a plan view of the apparatus of FIGS. 21 to 24.

The construction of the catch 169 is illustrated in FIG. 25 which shows three circumferentially spaced feet 181 which are connected to the piston 162 by legs 182 such that the feet normally engage a supporting annular track 183 attached to the cap 151. The track 183 is provided with cut-outs 184 into which the feet 181 fall to release the catch 169 when the cap is rotated to its final position.

During rotation of the cap 151 relative to the base portion 152 the cap is advanced axially by screw action. In order to prevent the piston 162 advancing until released by the catch 169 the track 183 is ramped to provide a compensating axial movement of the piston relative to the cap so that the piston remains stationary relative to the base portion 152.

Figure 26:
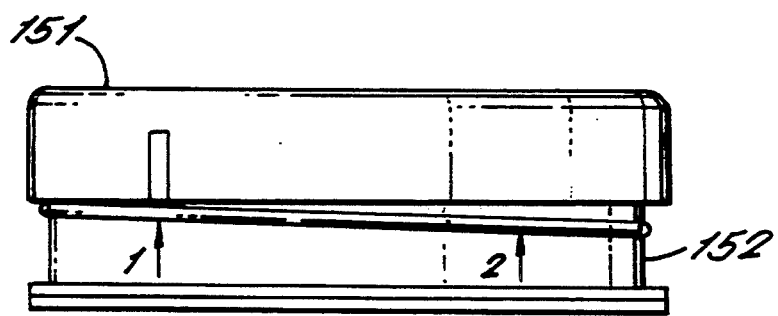
FIG. 26 is a side elevation of the apparatus of FIGS. 21 to 25.

Rotation of the cap 151 relative to the base portion 152 is stepped by use of suitable snap fitting detents and corresponding recesses (not shown) on the cap and base portion respectively. As shown in FIG. 26, suitable markings are provided on the cap 151 and base portion 152 to indicate the sequential steps of rotation.

Figure 29:
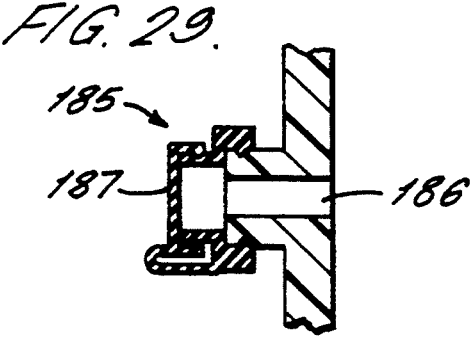
FIG. 29 is a section showing detail of an alternative drug injection port for use with the apparatus of FIGS. 21 to 26.

The drug insertion port 175 may be replaced by a drug filling port 185 of the type shown in FIG. 29 in which a duct 186 is normally closed by a hinged snap fitting closure 187. Drug is therefore introduced into the reservoir 160 by opening the closure 187, pouring the drug in and replacing the closure.

Figure 28:
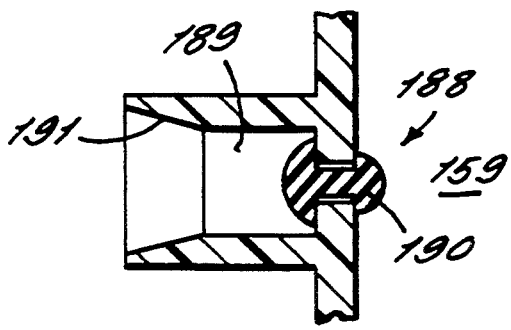
FIG. 28 is a section showing detail of a suction port valve of the apparatus of FIGS. 21 to 27.

The space 159 may be provided with a partial vacuum at manufacture or alternatively the partial vacuum within the space 159 may be produced immediately before use by withdrawing air through a suction port 188 of the type shown in FIG. 28. Suction port 188 comprises a duct 189 communicating with the space 159 via a non-return valve 190, the duct 189 being defined by a Luer connector 191 into which the hub of a syringe can be sealingly inserted. Suction created by reverse actuation of the syringe will thereby withdraw air through the non-return valve 190 from the space 159 to create a partial vacuum. The syringe is withdrawn from the connector 191 and the cell 158 is then sealed automatically by action of the valve 190 before attachment of the housing 153 to the skin.

Figure 30:
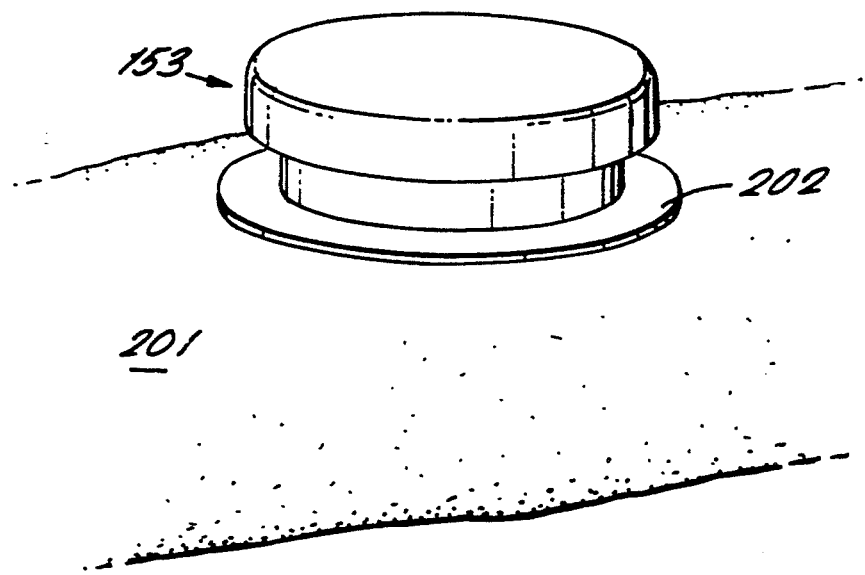
FIG. 30 is a perspective view of the apparatus of FIGS. 21 to 28 showing attachment to an arm of a patient.
Figure 31:
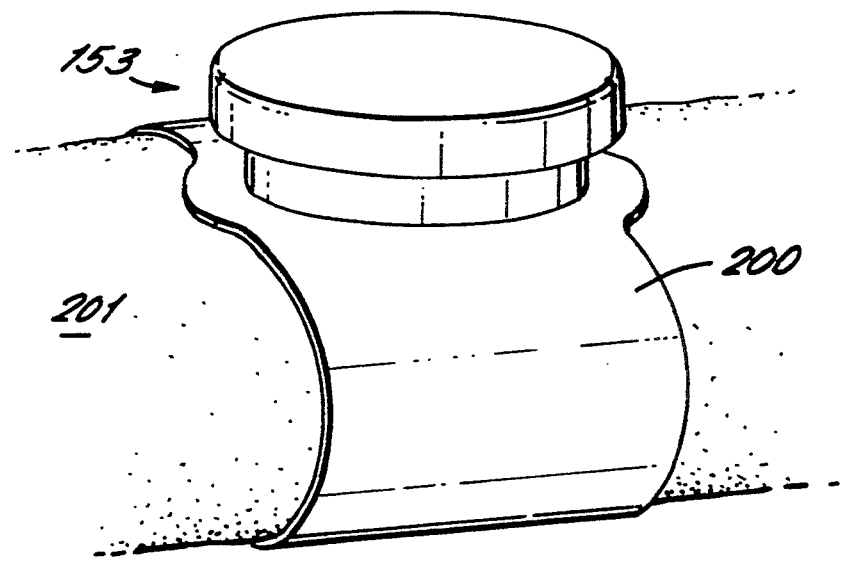
FIG. 31 is a perspective view of the apparatus of FIGS. 21 to 28 showing an alternative means of attachment to an arm of a patient.

The housing 153 may be attached to the skin of an arm or leg in the manner shown in FIG. 31 where an adhesive strip 200 extends around the limb 201. Alternatively as shown in FIG. 30 an annular adhesive film 202 may attach the housing 153 to a localised area of skin thereby contributing to the airtight seal formed between the disc portion 154 and the skin but without any further means of holding the housing in situ.

Figure 32:
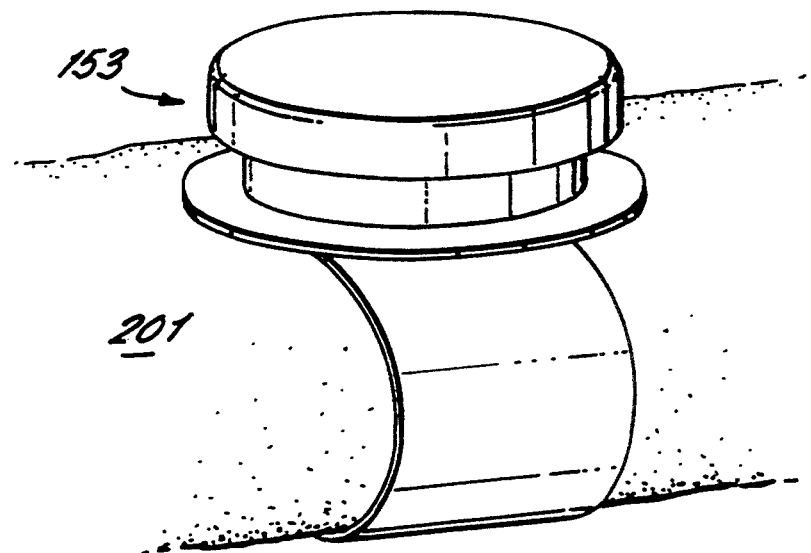
FIG. 32 is a perspective view of the apparatus of FIGS. 21 to 28 showing a further alternative means of attachment to the arm of a patient.
Figure 33:
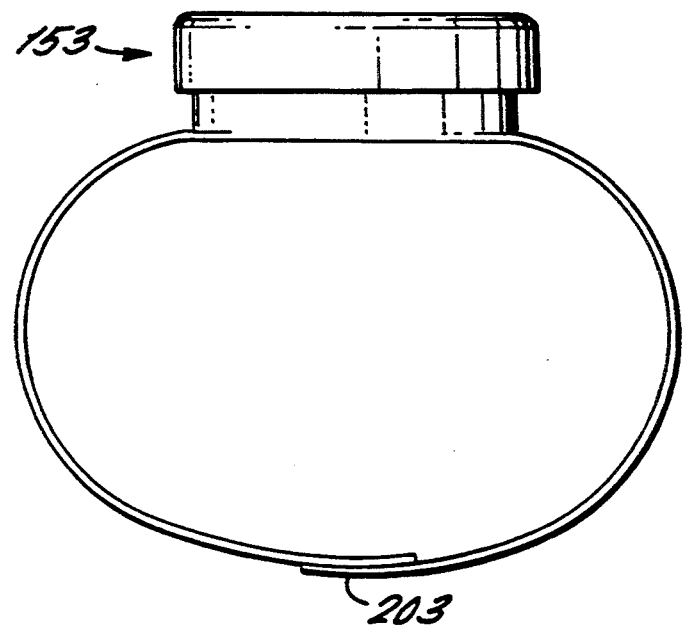
FIG. 33 is an elevation of the apparatus of FIG. 32.

As shown in FIG. 32 the arrangement of FIG. 30 can be supplemented by the addition of a strap fastened using a hook-loop fastener 203 as illustrated in FIG. 33.

In the above embodiments the adhesive used in contact with the skin may be of a hydrocolloidal type composed of pectin and gelatine or may alternatively be composed of acrylic or silicon. In each case the apparatus may be supplied with the adhesive covered in a protective sheet which also seals the aperture formed in the contact surface and the entire assembly can be sterilised in readiness for use.

The fifth apparatus 60 of FIGS. 7 and 8 may be provided with alternative means of expanding the chamber 63. For example a screw type arrangement or piston arrangement may be used to expand the enclosed chamber.

The contact surface may be sealed to the skin other than by the use of adhesive if required. For example the contact surface may be provided with projecting ribs which sealingly engage the skin surface and in such an arrangement the apparatus should be held firmly in place for example by straps.

Apparatus in accordance with the present invention may be provided with more than one evacuated cell to allow the partial vacuum to be re-established for example for the purpose of removing a self-healed epidermal barrier or to remove by suction any blister fluid within the chamber.

It may be desirable to provide apparatus in which the contact surface is interchangeable to provide apertures of different size.

The size of the de-epithelialised area of skin may also be stretched by applying stretching means to the surrounding skin.

In the examples referred to above the aperture size of 5 mm may be varied typically in the range 1 mm to 10 mm.

The drug may be applied in a form producing slow release, for instance by reversible binding in absorbent biodegradable starch particles, polymer(s), in non-biodegradable polysaccharide spheres, or in microcapsules consisting for instance partly of lipids or polymers of different types which may break or disintegrate slowly in biological fluids.

The drug may be applied in so-called pro-drug form, allowing it to pass through the tissue into the blood with minimal break-down (this being an important aspect in peptide delivery).

The re-epithelialisation of the drug delivery site can be delayed for instance by applying a steroid drug in addition to the therapeutic agent. Other means, for instance addition of antibodies to epithelial cells, may be used for the same purpose. The apparatus could be pre-loaded with such an agent, it could be added to the drug solution or taken by other routes.

The apparatus of FIGS. 1 to 6, 14 to 20 may be provided with a suction valve of the type described with reference to FIG. 28.

The apparatus of FIGS. 17 to 20 and of FIGS. 21 to 26 may be modified to include an expansion means of the type described with reference to FIG. 7. The apparatus may also optionally include a valve for interrupting the delivery of drug in use.

In the above embodiments reference is made to the delivery of drugs in liquid form. The apparatus may also be used to deliver gels and creams with suitable modification where appropriate.

Throughout the description and claims the term perfusion should be understood to encompass both the partial and complete diffusion of a fluid through body tissue i.e. including the partial diffusion of a fluid in which certain molecules contained in the fluid are diffused through tissue leaving a residue of undiffused fluid.

I claim:

1. Apparatus for use in transdermal perfusion of fluids through the skin of the human or animal body, the apparatus comprising a housing attachable to the body and having a contact surface which in use is held in contact with a portion of skin, the housing defining a chamber and the contact surface defining an aperture communicating with the chamber, and fluid supply means operable during a perfusion phase of operation of the apparatus to supply fluid to the chamber wherein the apparatus further comprises de-epithelializing means for removing a portion of the skin's epidermis from the skin's underlying dermis, the de-epithelializing means being operable during a preparatory phase of operation of the apparatus to expose an area of dermis of the skin at a treatment site which is accessible via the aperture such that subsequently during the pension phase direct contact is made between fluid in the chamber and the dermis.

2. Apparatus as claimed in claim 1 wherein the de-epithelialising means comprises suction means operable to form a partial vacuum in the chamber during a blister forming period in which an area of epithelium of the skin of the treatment site is separated from the dermis.

3. Apparatus as claimed in claim 2 wherein the housing is cooperable with the skin to form a closed compartment of which the chamber constitutes at least a part and comprises sealing means operable between the contact surface an annular area of skin peripheral to the treatment site whereby the partial vacuum is maintainable by substantially preventing the ingress of air during the blister forming period.

4. Apparatus as claimed in claim 3 wherein the suction means comprises a cell defining a space within which a partial vacuum is formed and disrupting means operable to disrupt a membrane partitioning the space from the chamber.

5. Apparatus as claimed in claim 4 wherein the cell is provided with a valve facilitating evacuation of air to create a partial vacuum within the space prior to operation of the disrupting means.

6. Apparatus as claimed in claim 3 comprising expanding means operable to expand the volume of the chamber to thereby create a partial vacuum.

7. Apparatus as claimed in any of claims 3 to 6 further comprising blister disruption means operable to open the suction blister by penetrating or removing the detached area of epithelium constituting a roof of the blister.

8. Apparatus as claimed in claim 7 comprising an actuator operable to sequentially actuate the suction means, the blister disruption means and by subsequent movement of the actuator to actuate the fluid supply means.

9. Apparatus as claimed in claim 8 wherein the actuator is operatively connected to a tubular member which is movable longitudinally in response to actuator movement so as to disrupt the membrane partitioning the space from the chamber to thereby initiate the blister forming period, the member being further longitudinally movable to a position in the chamber in which it disrupts the blister and the member further defining a longitudinal bore through which fluid is supplied to the chamber during the perfusion phase.

10. Apparatus as claimed in any of claims 3 to 6, 8 or 9 wherein the sealing means comprises an adhesive layer operable to sealingly secure the contact surface to an annular area of skin peripheral to the treatment site.

11. Apparatus as claimed in any of claims 3 to 6, 8 or 9 wherein the fluid supply means includes flow restricting means operable to restrict the flow of fluid into the chamber to a predetermined rate.

12. Apparatus for use in the formation of a suction blister on the skin of the human or animal body, the apparatus comprising a housing, means for attaching the housing to the body, the housing having a contact surface which in use is held in sealing contact with the skin, the housing defining a chamber and the contact surface defining an aperture communicating with the chamber, and the apparatus further comprising suction means operable to form a partial vacuum in the chamber and thereby form a suction blister at a treatment site which is accessible via the aperture, the housing being cooperable with the skin to form a closed airtight compartment of which the chamber constitutes at least a part, the chamber shape being such as to allow a suction blister to form in the chamber by delamination of the skin at the treatment site and by comprising sealing means operable between the contact surface and an annular portion of skin peripheral to the treatment site whereby the partial vacuum is maintainable by substantially preventing the ingress of air during a blister forming period.

13. Apparatus as claimed in claim 12 wherein the suction means comprises a cell defining a space within which a partial vacuum is formed and disrupting means operable to disrupt a membrane partitioning the space from the chamber.

14. Apparatus as claimed in claim 13 wherein the cell is provided with a valve facilitating evacuation of air to create a partial vacuum within the space prior to operation of the disrupting means.

15. Apparatus as claimed in claim 12 comprising expanding means operable to expand the volume of the chamber to thereby create a partial vacuum.

16. Apparatus as claimed in any of claims 12 to 15 further comprising blister disruption means operable to open the suction blister by penetrating a detached area of epidermis constituting a roof of the blister.

17. Apparatus as claimed in claim 16 wherein the disrupting means of the suction means comprises a member extending into the closed compartment and connected to an actuator located externally of the compartment, the member being movable from a rest position into a first position in which the member actuates the suction means and a second position in which the member disrupts the blister.

18. Apparatus as claimed in claim 16 wherein the sealing means comprises an adhesive layer operable to sealingly secure the contact surface to an annular area of skin peripheral to the treatment site.

19. A method of transdermal perfusion of fluids through the skin of the human or animal body, comprising the steps of attaching a housing to the body such that a contact surface of the housing is held in contact with a portion of skin, the housing defining a chamber and the contact surface defining an aperture communicating with the chamber, and operating a fluid supply means during a perfusion phase of operation to supply a quantity of fluid to the chamber, further comprising the step of de-epithelialization whereby a portion of the skin's epidermis is removed from the skins's underlying dermis during a preparatory phase of operation of the apparatus to expose an area of dermis of the skin at a treatment site which is accessible via the aperture such that subsequently during the perfusion phase direct contact is made between fluid in the chamber and the dermis.

20. A method as claimed in claim 19 wherein the step of de-epithelialisation comprises the operation of suction means to form a partial vacuum in the chamber during a blister forming period in which an area of epithelium of the skin at the treatment site is separated from the dermis and subsequently penetrating or removing the detached area of epithelium constituting the roof of the blister.

21. A method as claimed in claim 20 wherein the housing is cooperable with the skin to form a closed compartment of which the chamber constitutes at least a part and including the step of applying sealing means between the contact surface and an annular area of the skin peripheral to the treatment site whereby the partial vacuum is maintained by substantially preventing the ingress of air during the blister forming period.

22. A method of forming a suction blister on the skin of the human or animal body, comprising the steps of attaching a housing to the body such that a contact surface of the housing is held in sealing contact with the skin, the housing defining a chamber and the contact surface defining an aperture communicating with the chamber, operating suction means to form a partial vacuum in the chamber and thereby applying suction to an area of skin at a treatment site that is accessible via the aperture, and maintaining the partial vacuum during a blister forming period of about two to three hours until a portion of the skin's epidermis becomes separated from the skin's underlying dermis by the formation of a suction blister, wherein the housing cooperates with the skin to form a closed compartment of which the chamber constitutes at least a part and by including the step of applying sealing means between the contact surface and an annular area of the skin peripheral to the treatment site prior to operation of the suction means whereby the partial vacuum is subsequently maintained by substantially preventing the ingress of air during said blister forming period.

23. A method as claimed in claim 22 including the further step of evacuating air from a cell defined by the housing to form a partial vacuum therein and sealing the cell prior to attaching the housing to the body, and operating the suction means to place the chamber in communication with the cell to thereby form a partial vacuum in the chamber.

24. Apparatus as claimed in claim 12 further comprising blister disruption means operable to open the suction blister by bursting the detached area of epidermis constituting a roof of the blister.

25. Apparatus as claimed in claim 12 further comprising blister disruption means operable to open the suction blister by removing the detached areas of epidermis constituting a roof of the blister.

* * * * *

REEXAMINATION CERTIFICATE (3330th)
United States Patent [19]
Svedman

[11] B1 5,441,490
[45] Certificate Issued Sep. 16, 1997

[54] TRANSDERMAL PERFUSION OF FLUIDS

[75] Inventor: Pal Svedman, Ostanvag 85 B, S-216 Malmo, Sweden, 19

[73] Assignee: Pal Svedman, Malmo, Sweden

Reexamination Request:
No. 90/004,289, Jun. 27, 1996

Reexamination Certificate for:
Patent No.: 5,441,490
Issued: Aug. 15, 1995
Appl. No.: 84,267
Filed: Nov. 23, 1993

[22] PCT Filed: Jan. 7, 1992
[86] PCT No.: PCT/EP92/00029
§ 371 Date: Nov. 23, 1993
§ 102(e) Date: Nov. 23, 1993
[87] PCT Pub. No.: WO92/11879
PCT Pub. Date: Jul. 23, 1992

[30] Foreign Application Priority Data

Jan. 9, 1991 [SE] Sweden ................................. 9100058
Apr. 8, 1991 [SE] Sweden ................................. 9101022

[51] Int. Cl.$^6$ ................................................. A61M 35/00
[52] U.S. Cl. ..................... 604/289; 604/290; 604/200; 128/743
[58] Field of Search ......................... 604/313–316, 604/115, 200, 201, 204, 289, 290, 29; 128/743

[56] References Cited

U.S. PATENT DOCUMENTS

| | | | |
|---|---|---|---|
| 3,069,868 | 12/1962 | Skopyk | 604/316 |
| 3,486,504 | 12/1969 | Austin | 604/289 |
| 3,625,217 | 12/1971 | Schmidt | 604/316 |
| 4,680,028 | 7/1987 | Stuart | 604/316 |

FOREIGN PATENT DOCUMENTS

| | | | |
|---|---|---|---|
| 0452097 | 5/1913 | France | 604/313 |
| 958719 | 3/1950 | France | 604/313 |
| 1048558 | 11/1966 | United Kingdom | 604/313 |

OTHER PUBLICATIONS

Langkjer et al., A Suction blister method that gives epidermal biopsies from mice of different ages, suitable for histologic studies of Langerhans cells, I: 75–77, 1987.

Leun et al. The Influence of Skin Temperature on Dermal–Epidermal Adherence: Evidence Compatible with a Highly Viscous Bond, Journal of Investigative Dermatology, 42–46, 1974.

Michel et al., A simple method for studying chemotaxis, vascular permeability and histological modifications induced by mediators of inflammation in vivo in man, British Journal of Dermatology, 61–66, 1985.

Larsen–Nyhus, Ellen, 1984 Oslo University, "Collection Of Interstitial Fluid BY Local Exposure To Subatmospheric Pressure", Thesis Oslo University, Jan. 1984.

*Primary Examiner*—Mark O. Polutta

[57] ABSTRACT

An apparatus is provided for removing a small area of epidermis from the skin to expose an intact area of dermis and subsequently deliver a liquid in contact with the exposed dermis. This method of delivery allows the rate of absorption of substances into the body to be enhanced by removal of the epidermis. A preferred embodiment removes the epidermis by forming a suction blister, the apparatus having a housing attached to the skin adhesively to define a chamber in which suction is applied. Suction is applied to the chamber without connection to an external source of suction by means of an evacuated cell separated from the chamber by a disruptable membrane. A tubular member is actuated to rupture the membrane, disrupt the blister and deliver liquid to the chamber in successive stages of operation of the apparatus.

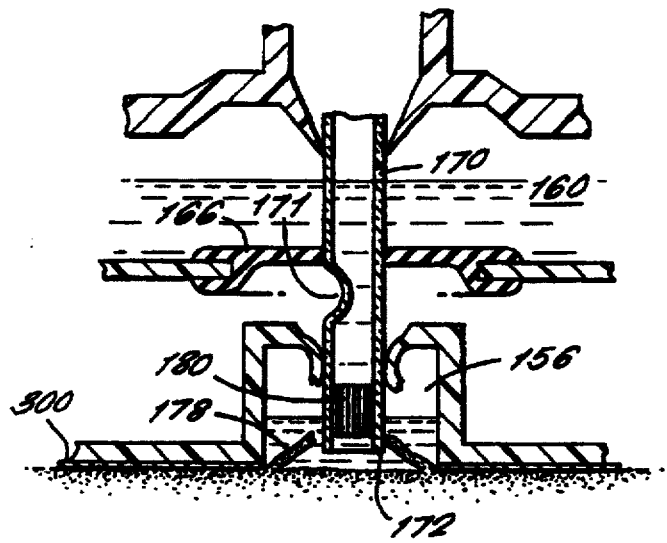

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 19–23 is confirmed.

Claims 1 and 12 are determined to be patentable as amended.

Claims 2–11, 13–18, 24 and 25, dependent on an amended claim, are determined to be patentable.

1. Apparatus for use in transdermal perfusion of fluids through the skin of the human or animal body, the apparatus comprising a housing attachable to the body and having a contact surface which in use is held in contact with a portion of skin, the housing defining a chamber and the contact surface defining an aperture communicating with the chamber, and fluid supply means operable during a perfusion phase of operation of the apparatus to supply fluid to the chamber wherein the apparatus further comprises de-epithelializing means for [removing a] *delaminating an intact portion of the skin's epidermis from the skin's underlying dermis*, the de-epithelializing means being operable during a preparatory phase of operation of the apparatus to expose an area of dermis of the skin at a treatment site which is accessible via the aperture such that subsequently during the [pension] *perfusion* phase direct contact is made between fluid in the chamber and the dermis.

12. Apparatus for use in the formation of a suction blister on the skin of the human or animal body, the apparatus comprising a housing, means for attaching the housing to the body, the housing having a contact surface which in use is held in sealing contact with the skin, the housing defining a chamber and the contact surface defining an aperture communicating with the chamber, and the apparatus further comprising suction means, *self-contained within said housing*, operable to form a partial vacuum in the chamber and thereby form a suction blister at a treatment site which is accessible via the aperture, the housing being cooperable with the skin to form a closed airtight compartment of which the chamber constitutes at least a part, the chamber shape being such as to allow a suction blister to form in the chamber by delamination of the skin at the treatment site *such that an intact portion of epidermis is delaminated from an area of dermis* and by comprising sealing means operable between the contact surface and an annular portion of skin peripheral to the treatment site whereby the partial vacuum is maintainable by substantially preventing the ingress of air during a blister forming period.

* * * * *